(12) United States Patent
Scofield et al.

(10) Patent No.: US 10,417,910 B2
(45) Date of Patent: Sep. 17, 2019

(54) DRIVING PROFILES FOR AUTONOMOUS VEHICLES

(71) Applicant: INRIX INC., Kirkland, WA (US)

(72) Inventors: Christopher L. Scofield, Seattle, WA (US); Scott Sedlik, Mercer Island, WA (US)

(73) Assignee: INRIX, Inc., Kirkland, WA (US)

(*) Notice: Subject to any disclaimer, the term of this patent is extended or adjusted under 35 U.S.C. 154(b) by 243 days.

(21) Appl. No.: 15/122,704

(22) PCT Filed: Mar. 2, 2015

(86) PCT No.: PCT/US2015/018285
§ 371 (c)(1),
(2) Date: Aug. 31, 2016

(87) PCT Pub. No.: WO2015/134376
PCT Pub. Date: Sep. 11, 2015

(65) Prior Publication Data
US 2017/0068245 A1    Mar. 9, 2017

Related U.S. Application Data

(60) Provisional application No. 61/946,962, filed on Mar. 3, 2014.

(51) Int. Cl.
*A61B 5/00* (2006.01)
*A61B 5/0205* (2006.01)
(Continued)

(52) U.S. Cl.
CPC ... *G08G 1/096791* (2013.01); *A61B 5/02055* (2013.01); *A61B 5/0476* (2013.01);
(Continued)

(58) Field of Classification Search
CPC ............ B60R 16/0232; B60R 16/0236; G05D 1/0016; G05D 1/0022; G05D 1/0027;
(Continued)

(56) References Cited

U.S. PATENT DOCUMENTS

| 6,216,086 B1* | 4/2001 | Seymour ............ G01C 21/3446 701/425 |
| 8,344,849 B2* | 1/2013 | Larsson .................. B60R 25/25 340/426.11 |

(Continued)

OTHER PUBLICATIONS

Corresponding International Application No. PCT/US15/18285, International Search report and written opinion dated Jun. 3, 2015.
(Continued)

*Primary Examiner* — Jerrah Edwards
(74) *Attorney, Agent, or Firm* — Cooper Legal Group, LLC

(57) ABSTRACT

One or more techniques and/or systems are provided for operating an autonomous vehicle based upon a driving preference. For example, a driving profile, comprising a driving preference (e.g., a speed preference, a route preference, etc.) of a user, may be provided to an automated driving component of the autonomous vehicle. An operational parameter for the autonomous vehicle may be generated based upon the driving preference of the user. The autonomous vehicle may be operated based upon the operational parameter. In an example, a condition of the user traveling in the autonomous vehicle may be determined, and the operational parameter for the autonomous vehicle may be adjusted based upon the condition of the user not corresponding to the driving preference.

20 Claims, 11 Drawing Sheets

(51) Int. Cl.

| | | |
|---|---|---|
| A61B 5/0476 | (2006.01) | |
| G01C 21/34 | (2006.01) | |
| G05D 1/00 | (2006.01) | |
| G05D 1/02 | (2006.01) | |
| H04B 1/3822 | (2015.01) | |
| H04L 29/08 | (2006.01) | |
| G08G 1/0967 | (2006.01) | |
| H04W 4/50 | (2018.01) | |
| G06N 20/00 | (2019.01) | |
| G06F 16/29 | (2019.01) | |
| G08G 1/01 | (2006.01) | |
| G08G 1/0968 | (2006.01) | |
| B60W 30/14 | (2006.01) | |
| G07C 5/00 | (2006.01) | |
| G08G 1/0965 | (2006.01) | |
| B64C 39/02 | (2006.01) | |
| G08G 1/097 | (2006.01) | |
| H04B 7/185 | (2006.01) | |
| G06Q 20/10 | (2012.01) | |
| G06Q 30/02 | (2012.01) | |
| G08G 1/07 | (2006.01) | |
| H04W 12/08 | (2009.01) | |
| H04M 15/00 | (2006.01) | |
| G06Q 40/08 | (2012.01) | |
| H04L 9/32 | (2006.01) | |
| B60R 16/023 | (2006.01) | |
| G07B 15/00 | (2011.01) | |
| G08G 1/0962 | (2006.01) | |
| H04W 4/04 | (2009.01) | |
| G08G 1/065 | (2006.01) | |
| G01C 21/36 | (2006.01) | |
| H04W 4/42 | (2018.01) | |
| B60W 40/08 | (2012.01) | |
| B60W 40/09 | (2012.01) | |
| G08G 1/09 | (2006.01) | |
| G07B 15/06 | (2011.01) | |
| H04W 4/40 | (2018.01) | |
| H04W 4/48 | (2018.01) | |
| A61B 5/024 | (2006.01) | |
| A61B 5/053 | (2006.01) | |
| G06Q 50/30 | (2012.01) | |

(52) U.S. Cl.
CPC ........ *A61B 5/4845* (2013.01); *B60R 16/0236* (2013.01); *B60W 30/143* (2013.01); *B60W 40/08* (2013.01); *B60W 40/09* (2013.01); *B64C 39/024* (2013.01); *G01C 21/3415* (2013.01); *G01C 21/3469* (2013.01); *G01C 21/3617* (2013.01); *G01C 21/3655* (2013.01); *G01C 21/3667* (2013.01); *G01C 21/3682* (2013.01); *G05D 1/0011* (2013.01); *G05D 1/0088* (2013.01); *G05D 1/021* (2013.01); *G06F 16/29* (2019.01); *G06N 20/00* (2019.01); *G06Q 20/102* (2013.01); *G06Q 30/0283* (2013.01); *G06Q 40/08* (2013.01); *G07B 15/00* (2013.01); *G07B 15/063* (2013.01); *G07C 5/008* (2013.01); *G08G 1/012* (2013.01); *G08G 1/0112* (2013.01); *G08G 1/0129* (2013.01); *G08G 1/0141* (2013.01); *G08G 1/0145* (2013.01); *G08G 1/065* (2013.01); *G08G 1/07* (2013.01); *G08G 1/093* (2013.01); *G08G 1/097* (2013.01); *G08G 1/0962* (2013.01); *G08G 1/0965* (2013.01); *G08G 1/0967* (2013.01); *G08G 1/096725* (2013.01); *G08G 1/096741* (2013.01); *G08G 1/096775* (2013.01); *G08G 1/096811* (2013.01); *G08G 1/096822* (2013.01); *G08G 1/096838* (2013.01); *H04B 1/3822* (2013.01); *H04B 7/18504* (2013.01); *H04L 9/3247* (2013.01); *H04L 67/02* (2013.01); *H04L 67/306* (2013.01); *H04M 15/60* (2013.01); *H04W 4/046* (2013.01); *H04W 4/40* (2018.02); *H04W 4/42* (2018.02); *H04W 4/50* (2018.02); *H04W 12/08* (2013.01); *A61B 5/024* (2013.01); *A61B 5/0531* (2013.01); *B60W 2040/0809* (2013.01); *B60W 2040/0872* (2013.01); *B60W 2540/22* (2013.01); *B60W 2550/12* (2013.01); *B60W 2550/14* (2013.01); *B60W 2710/1044* (2013.01); *B60W 2710/18* (2013.01); *B60W 2720/10* (2013.01); *B64C 2201/123* (2013.01); *G01C 21/3608* (2013.01); *G06Q 50/30* (2013.01); *G06Q 2240/00* (2013.01); *H04W 4/48* (2018.02)

(58) Field of Classification Search
CPC .. G05D 1/0055; G05D 1/0061; G05D 1/0066; G05D 1/0088; G05D 1/02; G05D 1/021; G05D 1/0212; G05D 1/0214; G05D 1/0217; G05D 1/0221; G05D 1/0223; G05D 1/0276; G05D 1/0287; G05D 1/0289; G06F 17/30241
See application file for complete search history.

(56) References Cited

U.S. PATENT DOCUMENTS

| | | | |
|---|---|---|---|
| 8,635,018 B2 * | 1/2014 | Chia | G07C 5/008 701/25 |
| 9,517,771 B2 * | 12/2016 | Attard | B60W 30/182 |
| 9,950,708 B1 * | 4/2018 | Cullinane | B60W 30/095 |
| 2003/0162523 A1 | 8/2003 | Kapolka et al. | |
| 2006/0178140 A1 | 8/2006 | Smith et al. | |
| 2007/0005609 A1 | 1/2007 | Breed | |
| 2007/0244614 A1 | 10/2007 | Nathanson | |
| 2008/0228365 A1 * | 9/2008 | White | B60K 28/063 701/70 |
| 2008/0252412 A1 * | 10/2008 | Larsson | B60R 25/25 340/5.2 |
| 2010/0157061 A1 | 6/2010 | Katsman et al. | |
| 2011/0251734 A1 | 10/2011 | Schepp et al. | |
| 2012/0083960 A1 | 4/2012 | Zhu et al. | |
| 2013/0204455 A1 * | 8/2013 | Chia | G07C 5/008 701/1 |
| 2013/0238170 A1 | 9/2013 | Klinger | |
| 2015/0149017 A1 * | 5/2015 | Attard | B60W 30/182 701/23 |
| 2017/0219364 A1 * | 8/2017 | Lathrop | G01C 21/3453 |

OTHER PUBLICATIONS

EP Communication cited in EP Application No. 15758684.3 dated Dec. 1, 2017, 15 pgs.

* cited by examiner

DRIVING PROFILES FOR AUTONOMOUS VEHICLES

A CROSS-REFERENCE TO RELATED APPLICATIONS

This application claims priority to U.S. Provisional Patent Application No. 61/946,962 titled "DETERMINING HOV/HOT LANE TRAVEL TIMES", filed on Mar. 3, 2014, which is hereby incorporated by reference.

BACKGROUND

Many users utilize vehicles that operate in an autonomous and/or a semi-autonomous manner (e.g., parking assist, lane assist, etc.). In an example, some autonomous vehicles have the ability to transport users from one location to another location with minimal to no user involvement. In doing so, autonomous vehicles may be configured to make a majority of the operational decisions for the user. However, many users may desire to have the ability to control various aspects of how the autonomous vehicle operates, such as those users that have been accustomed a certain driving style, route, driving speed, etc. Unfortunately, users may not be able to efficiently and/or effectively control such operational aspects. As a result, autonomous vehicles may leave users feeling as if they have little to no control over the manner in which the autonomous vehicles operates.

SUMMARY

This summary is provided to introduce a selection of concepts in a simplified form that are further described below in the detailed description. This summary is not intended to identify key factors or essential features of the claimed subject matter, nor is it intended to be used to limit the scope of the claimed subject matter.

Among other things, one or more systems and/or techniques for operating an autonomous vehicle are provided herein. In an example, a driving profile, comprising a driving preference (e.g., a speed preference, a route preference, etc.) of a user, may be received by an automated driving component of the autonomous vehicle. In an example, the driving profile may be received, through a communication connection (e.g., Wi-Fi connection, Bluetooth connection, a cellular connection, etc.), from a remote driving preference provider (e.g., a storage component hosted on a cloud based server and/or a mobile device configured to store and/or provide access to driving profiles of the user). The driving profile may be evaluated to identify the driving preference of the user. An operational parameter for the autonomous vehicle may be generated based upon the driving preference of the user. In an example, a route to a destination may be generated based upon the driving preference. The autonomous vehicle may be operated based upon the operational parameter. In an example, the autonomous vehicle may be operated to travel along the route based upon the operational parameter (e.g., maintain a particular speed with respect to a posted speed limit; avoid bridges; avoid lane changes; etc.).

In an example, a condition of the user traveling in the autonomous vehicle may be determined (e.g., is the user calm, is the user stressed, etc.). The condition may be determined by evaluating biometric data corresponding to the user. In an example, the biometric data may comprise heartrate data, body temperature data, skin conductance data, voice stress level data, brainwave data, and/or blood alcohol level data. The operational parameter for the autonomous vehicle may be adjusted in response to the condition of the user not corresponding to the driving preference of the user (e.g., determining if the condition of the user corresponds to a condition associated with the driving preference; by way of example, a low stress state may be associated a low speed preference or a high speed preference may be associated with an emotionally high state). In another example, the route to the destination may be adjusted to generate an adjusted route in response to the condition of the user not corresponding to the driving preference of the user (e.g., the route may be adjusted based upon the condition of the user indicated the user is becoming stressed as a result of being stuck in traffic).

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

Figure 1:
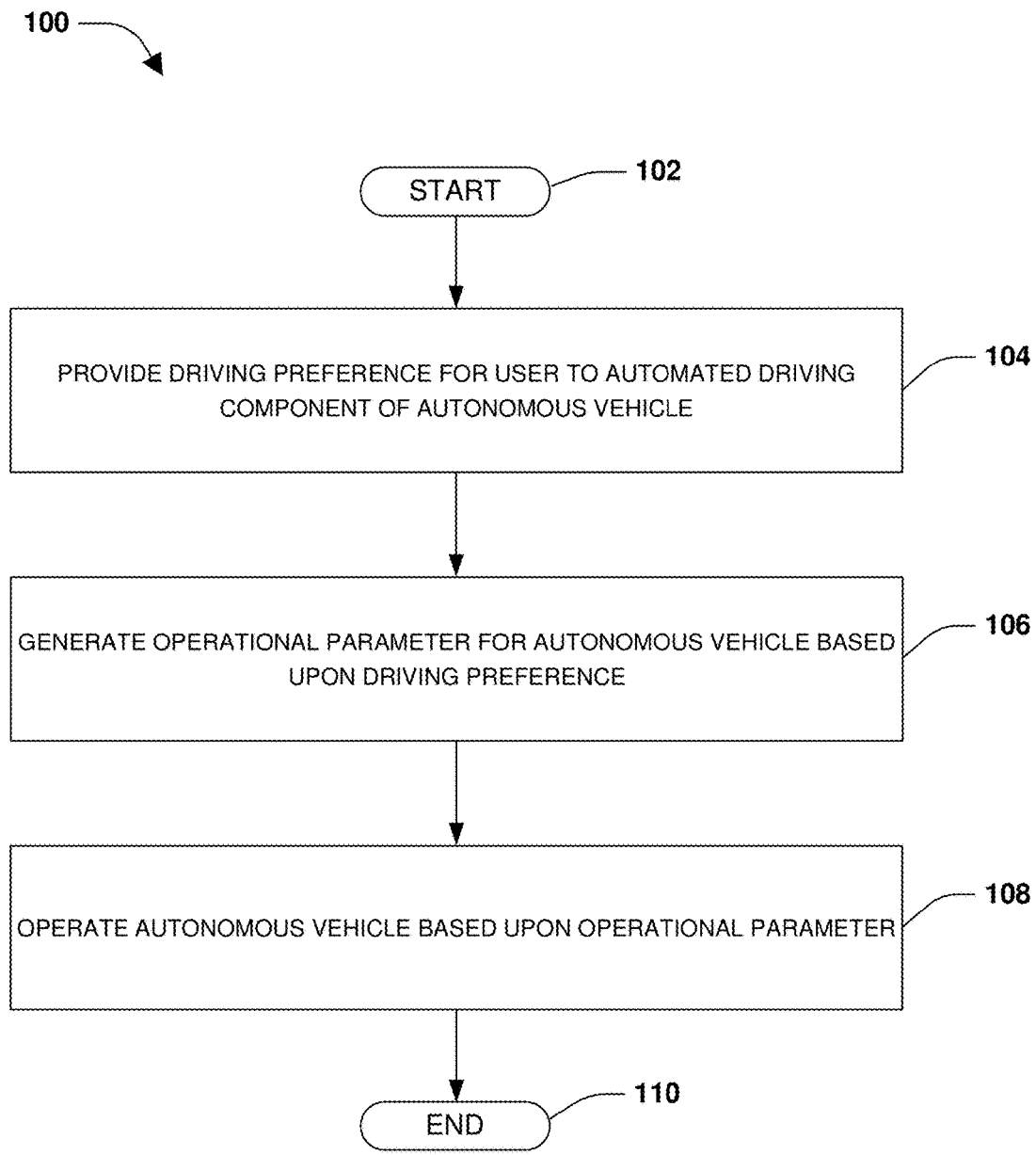
FIG. 1 is a flow diagram illustrating an exemplary method of operating an autonomous vehicle.

The claimed subject matter is now described with reference to the drawings, wherein like reference numerals are generally used to refer to like elements throughout. In the following description, for purposes of explanation, numerous specific details are set forth to provide an understanding of the claimed subject matter. It may be evident, however, that the claimed subject matter may be practiced without these specific details. In other instances, structures and devices are illustrated in block diagram form in order to facilitate describing the claimed subject matter.

One or more systems and/or techniques for operating autonomous vehicles are provided herein. Users may have a desire to control the manner in which autonomous vehicles are operated, such by adjusting an operational speed, a tailgating distance (e.g., bumper to bumper distance between two cars), a fuel performance characteristic, etc. of autonomous vehicles. Unfortunately, such control capabilities may not be available in autonomous vehicles, and control systems that operate autonomous vehicles may lack technology for allowing users to adequately customize how the autonomous vehicle operates. As provided herein, a driving preference (e.g., a route preference, a speed preference, a full consumption preference, a tailgating preference, a lane preference, etc.) of a user may be provided to an automated driving component of an autonomous vehicle. An operational parameter for the autonomous vehicle may be generated based upon the driving preference of the user. The autonomous vehicle may be operated based upon the operational parameter (e.g., the operational parameter may be used to control the operation of the autonomous vehicle, such that the autonomous vehicle operates and/or performs in accordance with the driving preference).

By providing functionality for controlling various aspects of the operation of autonomous vehicles, users may be able to better utilize the functionality of autonomous vehicles, as well as benefit from an enhanced user experience therewith. For example, with increased control over the operation of autonomous vehicles, users may be able to more effectively and efficiently operate autonomous vehicles based upon the needs of a user and/or the functionality the user may desire to optimize (e.g., increased fuel economy for long drives, increased power output when hauling heavy loads, increased tailgating distance on icy roads, reducing stress by avoiding high traffic routes, etc.). Accordingly, operating efficiency, functionality, and/or power consumption of autonomous vehicles may be improved and more fully utilized by providing users with an increased ability to control autonomous vehicles, such as through the use of driving profiles. Furthermore, by maintaining driving profiles on a remote preference provider, users may be able to efficiently store, update, and/or transfer custom driving profiles from one autonomous vehicle to another autonomous vehicle without the need to recreate the driving profile. In this way, the driving profile of the user may be conveniently and efficiently utilized on one or more autonomous vehicles.

An embodiment of operating an autonomous vehicle is illustrated by an exemplary method 100 of FIG. 1. At 102, the method 100 starts. At 104, a driving preference of a user may be provided to an automated driving component of an autonomous vehicle. The driving preference may be comprised within a driving profile of the user. The driving profile may comprise a set of driving preferences specified by the user (e.g., a custom driving profile). The set of driving preferences may be configured to tailor a driving experience for the user.

In an example of providing the driving preference, the driving profile may be selected, such as manually by the user and/or automatically by the automated driving component (e.g., the automated driving component may access a calendar of the user to identify an event time and location, and select the driving profile that will enable the user to arrive to the event on time or in a manner desired by the user for traveling to such an event). The driving profile may comprise a cautious profile, a shortest duration profile, a shortest distance profile, a leisurely profile, a driving enthusiast profile, a fuel economy profile, a scenic profile, a sightseeing profile, a weather profile, etc.

In an example, the driving profile may be evaluated to identify the driving preference. The driving preference may comprise a route preference (e.g., a scenic route preference, a shortest route preference), a speed preference (e.g., a speed equal to a speed limit, a speed 5 mph under the speed limit, a speed that is 10% under the speed limit, a speed equal to other cars traveling a route, a speed within a speed range, etc.), a lane preference (e.g., a right lane preference, a left lane preference, a carpool lane preference, an express pay lane preference, etc.), a tailgating preference (e.g., the user may prefer to maintain a minimum tailgating distance based upon the speed being traveled and/or a set tailgating distance, such as four car lengths regardless of speed, etc.), a turn preference (e.g., the user may prefer to avoid left hand turns, right hand turns at red lights, etc.), a traffic level preference (e.g., a traffic avoidance preference), a traffic control device preference (e.g., the user may prefer to avoid red lights, stop signs, etc.; the user may prefer to stop at yellow lights; etc.), a performance preference (e.g., a fuel performance preference), etc.

By way of example, the route preference may comprise a high speed route preference (e.g., the user may indicate a preference for routes with speed limits above 55 mph), a low speed route preference (e.g., the user may indicate a preference for routes on surface roads with speed limits below 40 mph), an aesthetic route preference (e.g., the user may indicate a preference for routes through parks, nature preserves, etc.), a safe route preference (e.g., the user may indicate a preference for routes that avoid roads, intersection, and/or areas with a historically high occurrence of accidents, etc.), a shortest distance route preference (e.g., the user may indicate a preference for a route with the shortest distance), a traffic flow route preference (e.g., the user may indicate a preference for routes that avoid historically high traffic areas, current traffic jams, stop lights, roundabouts, construction zones, etc.), a route terrain preference (e.g., the user may indicate a preference for routes along flat roads; the user may indicate a preference for routes which avoid hilly regions; the user may indicate a preference to avoid routes where pot holes have been reported by other users; etc.), a traffic enforcement route preference (e.g., the user may indicate a preference for routes that avoid red light cameras or area's highly patrolled by law enforcement officers; the user may indicate a preference for routes that include speed cameras to reduce the likelihood that other drivers will be speeding; etc.). In another example, the performance preference may comprise a fuel performance preference (e.g., the user may indicate a preference to operate the autonomous vehicle to maximize fuel performance, such as by firing less cylinders when traveling a long distances on a highway, etc.), an environmental performance preference (e.g., the user may indicate a preference to operate the vehicle such that $CO_2$ emissions are reduced, etc.), a sports performance preference (e.g., the user may indicate a preference to operate the vehicle such that handling, acceleration, and/or torque are maximized), etc.

In an example, the driving profile and/or the driving preference may be provided from a remote preference provider to the automated driving component. The remote preference provider may be hosted on a cloud-based server, a mobile device of the user (e.g., a smartphone, a tablet, a smart watch, etc.), and/or an in-vehicle human machine interface. In an example of providing the driving profile, a communication connection (e.g., a Wi-Fi connection, a Bluetooth connection, a cellular connection, etc.) may be created to provide the driving profile from the remote preference provider to the automated driving component. In this way, the driving profile may be conveniently and efficiently utilized by one or more autonomous vehicles (e.g., the driving profile may be provided to a personal autonomous vehicle of the user, a work autonomous vehicle of the user, and/or a family member's autonomous vehicle that the user is borrowing).

In an example of providing the driving profile, a calendar, an email client, a webpage, a social media profile, and/or a mobile application of the user may be assessed to identify event information for an event. The event information may comprise an event location, an event time, an event type (e.g., a work meeting, birthday party, doctor appointment, flight departure, etc.), and/or an event priority. The event information may be evaluated to select the driving profile based upon at least one of the event location, the event time, the event type, and/or the event priority. For example, responsive to determining that a business event having a high priority begins in 12 minutes, a driving profile may be selected that will enable the user to arrive at the event on time based upon the location of the event.

At 106, an operational parameter for the autonomous vehicle may be generated based upon the driving preference. The operational parameter may be utilized by the automated driving component to determine a manner in which the autonomous vehicle should perform under various conditions and/or in response to various events. The operational parameter may be configured based upon a characteristic of the autonomous vehicle (e.g., vehicle length, width, weight, braking ability, acceleration, turning radius, fuel range, etc.). In an example, the operational parameter may be utilized to determine a response for the autonomous vehicle as a result to a change in a driving condition (e.g., determine an amount of braking necessary to maintain a tailgating distance in response to a change in speed of a second vehicle traveling in front of the autonomous vehicle, determine a speed adjustment to safely operate the autonomous vehicle in response to a change in weather, determine a speed adjustment in response to a change in speed limit along a route, etc.).

In an example, a set of operational parameters may be generated based upon a set of driving preferences within the driving profile. A priority value may be determined for individual operational parameters within the set of operational parameters (e.g., operational parameters are assigned a priority value based upon the importance of the operational parameters to the user). The operational parameters within the set of operational parameters may be ranked to generate a ranked set of operational parameters. In an example, the operational parameters may be ranked based upon their priority value. The autonomous vehicle may be operated based upon the ranked set of operational parameters. For example, responsive to a maximum speed limit operational parameter being ranked higher than a right lane operational parameter, the automated driving component may direct the autonomous vehicle into the left lane as a result of a second vehicle traveling in the right lane at a speed under the speed limit.

At 108, the autonomous vehicle may be operated based upon the operational parameter. In an example, a route to a destination may be generated based upon the driving preference for the user and/or the operational parameter of the autonomous vehicle. Responsive to generating the route to the destination, the autonomous vehicle may be operated to travel the route based upon the operational parameters for the user. In an example, the operational parameter may be utilized to operate the autonomous vehicle in accordance with the driving preference (e.g., if the user prefers the autonomous vehicle be operated at speeds below the speed limit, the operational parameter may be utilized by the automated diving component to adjusted the speed of the autonomous vehicle as it travels across roads having various speed limits).

In an example, a condition of the user traveling within the autonomous vehicle may be determined (e.g., the user may be in a high stress state as a result of being stuck in traffic). The condition of the user may be determined by evaluating biometric data corresponding to the condition of the user. In an example, one or more biometric sensors may be utilized to obtain biometric data for the user (e.g., a smart watch worn by the user may collect heartrate data of the user, a conductive sensor in a surface of steering wheel may collect skin conductance data related to a perspiration level of the user, etc.). The biometric data may comprise heartrate data, body temperature data, skin conductance data (e.g., galvanic skin response data, electrodermal response data, psychogalvanic reflex data, skin conductance response data, etc.), voice stress analysis data, brainwave data (e.g., electroencephalography data), blood alcohol content data, etc. In another example, the user may provide the condition to the automated driving component though an interaction with a user interface (e.g., an interface displayed by a mobile device, a webpage, an in-vehicle human machine interface, a voice input or instruction, etc.).

In an example, the operation of the autonomous vehicle may be adjusted based upon the condition of the user. For example, responsive to the condition of the user not corresponding to a conditional state associated with the driving preference of the user, the operational parameter for the autonomous vehicle may be adjusted (e.g., if the user selected a low speed preference associated with a low stress state and the condition of the user is indicative of a high stress state, the operating speed of the autonomous vehicle may be adjusted to a lower speed). In another example, responsive to the condition of the user not corresponding to the driving preference, an adjusted route to the destination may be generated (e.g., if the user selected a high speed preference associated with a medium stress level and the user is experiencing a high stress state as a result of being stuck in traffic, the automated driving component may generate an adjusted route allowing for a faster rate of travel). The autonomous vehicle may be operated by the automated driving component to travel along the adjusted route to the destination based upon the operational parameter.

In an example, the user may be identified as entering a second autonomous vehicle. The driving preference (or driving profile) for the user may be provided to a second automated driving component of the second autonomous vehicle in response to the user entering the second autonomous vehicle (e.g., the driving profile of the user may travel with the user from autonomous vehicle to autonomous vehicle). For example, if the user rents an autonomous vehicle in another city, the driving profile for the user may be downloaded to the rented autonomous vehicle. In an example, the driving preference may be provided from the remote preference provider. A second operational parameter for the second autonomous vehicle may be generated based upon the driving preference and/or a second characteristic of the second autonomous vehicle. The second autonomous vehicle may be operated by the second automated driving component based upon the second operational parameter.

In an example, the user may provide feedback to the automated driving component. The feedback may provide an indication of whether the autonomous vehicle is operated as the user intended based upon the driving profile selected. The feedback may be utilized by the automated driving component to modify the operational parameters corresponding to the feedback. In an example, the feedback may be provided to the automated driving component in real time. The feedback may comprise an activity record of adjustments suggested and/or made to the operation of the autonomous vehicle by the user (e.g., responsive to a cautious driving profile being selected and the user reducing the speed of the autonomous vehicle, feedback may be provided indicating that the speed of the autonomous vehicle was greater than desired by the user). In another example, the feedback may be provided as a set of operational features. The set of operational features may be extracted from vehicle data collected while the automated driving component operated the autonomous vehicle along the route. In an example of extracting an operational feature, fuel consumption data collected at various speeds along the route may be indicative of an optimal speed for operating the autonomous vehicle along the route and/or a similar route (e.g., fuel usage data illustrating a fuel usage rate of 21 mpg at 65 mph and a fuel usage rate of 24 mpg at 55 mph may be indicative that it is more fuel efficient to operate the autonomous vehicle at 55 mph rather than at 65 mph). In another example of extracting an operational feature, heart rate data of the user collected at various points along the route may be indicative of an optimal tailgating distance for the user (e.g., heartrate data illustrating the user's heartrate was 60 bpm when the tailgating distance was 35 feet and 120 bpm when the tailgating distance was 10 feet, which may be indicative that the user prefers the 35 foot tailgating distance). In an example, the feedback from the user may be utilized to train an operational parameter model of the automated driving component. At 110, the method ends.

Figure 2:
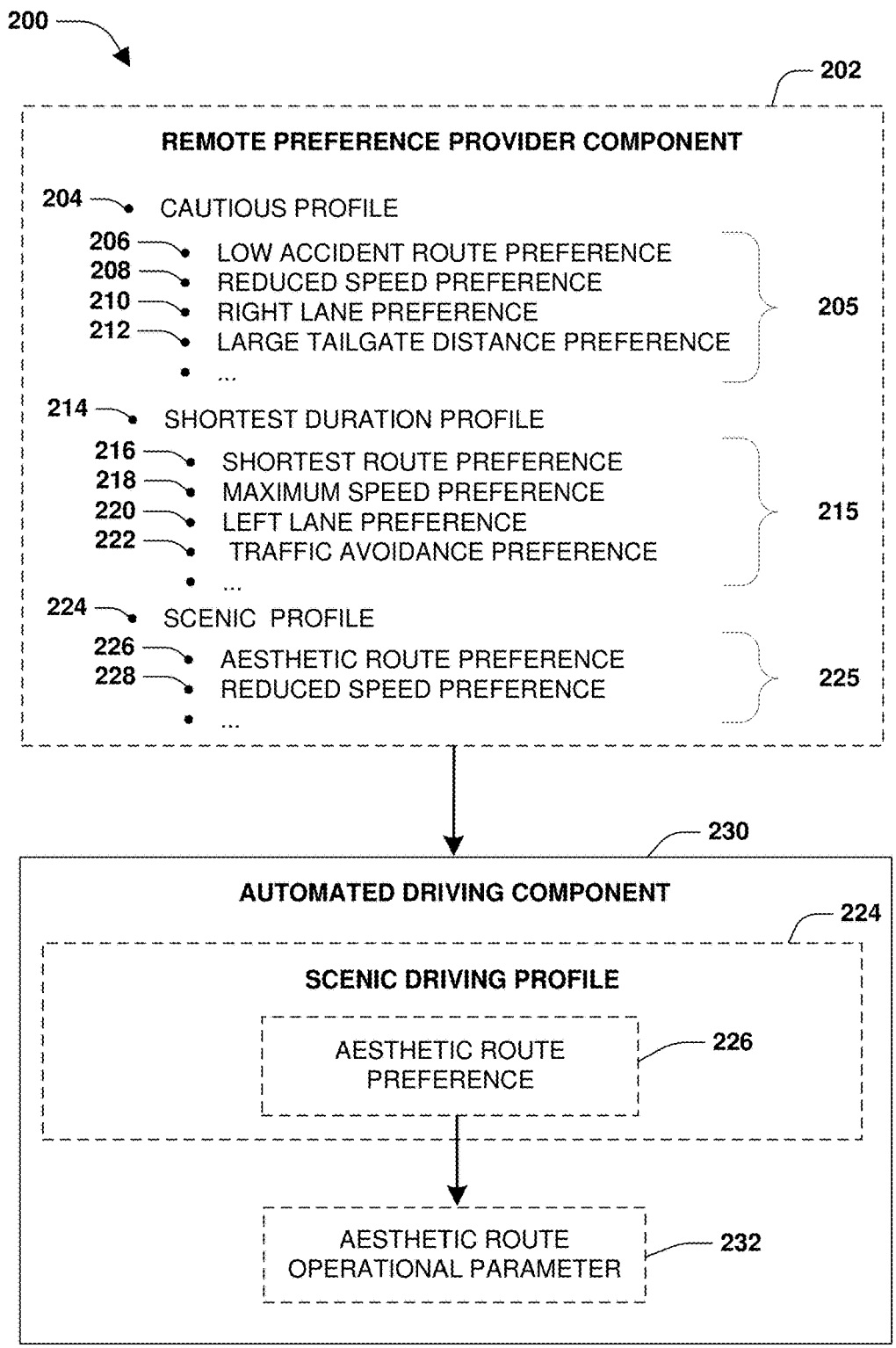
FIG. 2 is a component block diagram illustrating an exemplary system for operating an autonomous vehicle.

FIG. 2 illustrates an example of a system 200 for operating an autonomous vehicle. The system 200 comprises a remote preference provider component 202 and/or an automated driving component 230. The remote preference provider component 202 may be configured to provide a driving profile, such as cautious profile 204, a shortest duration profile 214, and/or a scenic profile 224, to the automated driving component 230. In an example, the cautious profile 204 may comprise a first set 205 of driving preferences 206-212, the shortest duration profile 214 may comprise a second set 215 of driving preferences 216-222, and/or the scenic profile 224 may comprise a third set 225 of driving preferences 226-228. The remote preference provider component 202 may provide a full set of driving preferences, a partial set of driving preferences, and/or an individual driving preference to the automated driving component 230. In an example, a user may utilize a user interface (not illustrated) to select the driving profile to be provided to the automated driving component 230. The user interface may be displayed by a mobile device and/or a display console of the autonomous vehicle.

In an example, responsive to the scenic profile 224 being selected, the automated driving component 230 may receive the scenic profile 224 from the remote preference provider component 202. The scenic profile 224 may be evaluated by the automated driving component 230 to identify the aesthetic route preference 226 from the scenic profile 224. An operational parameter, such as an aesthetic route operational parameter 232 may be generated by the automated driving component 230 based upon the aesthetic route preference 226. The automated driving component 230 may be configured to operate the autonomous vehicle based upon the aesthetic route operational parameter 232. For example, the automated driving component 230 may configure the autonomous vehicle to travel along a longer route through a park rather than a shorter route through an industrial area based upon the aesthetic route operational parameter 232. In another example, the user may select a plurality of driving preferences and/or generate a plurality of operational parameters to control various aspect of the autonomous vehicle. In this way, the user may have more control over the operation of autonomous vehicles and thus a driving experience may be improved.

Figure 3A:
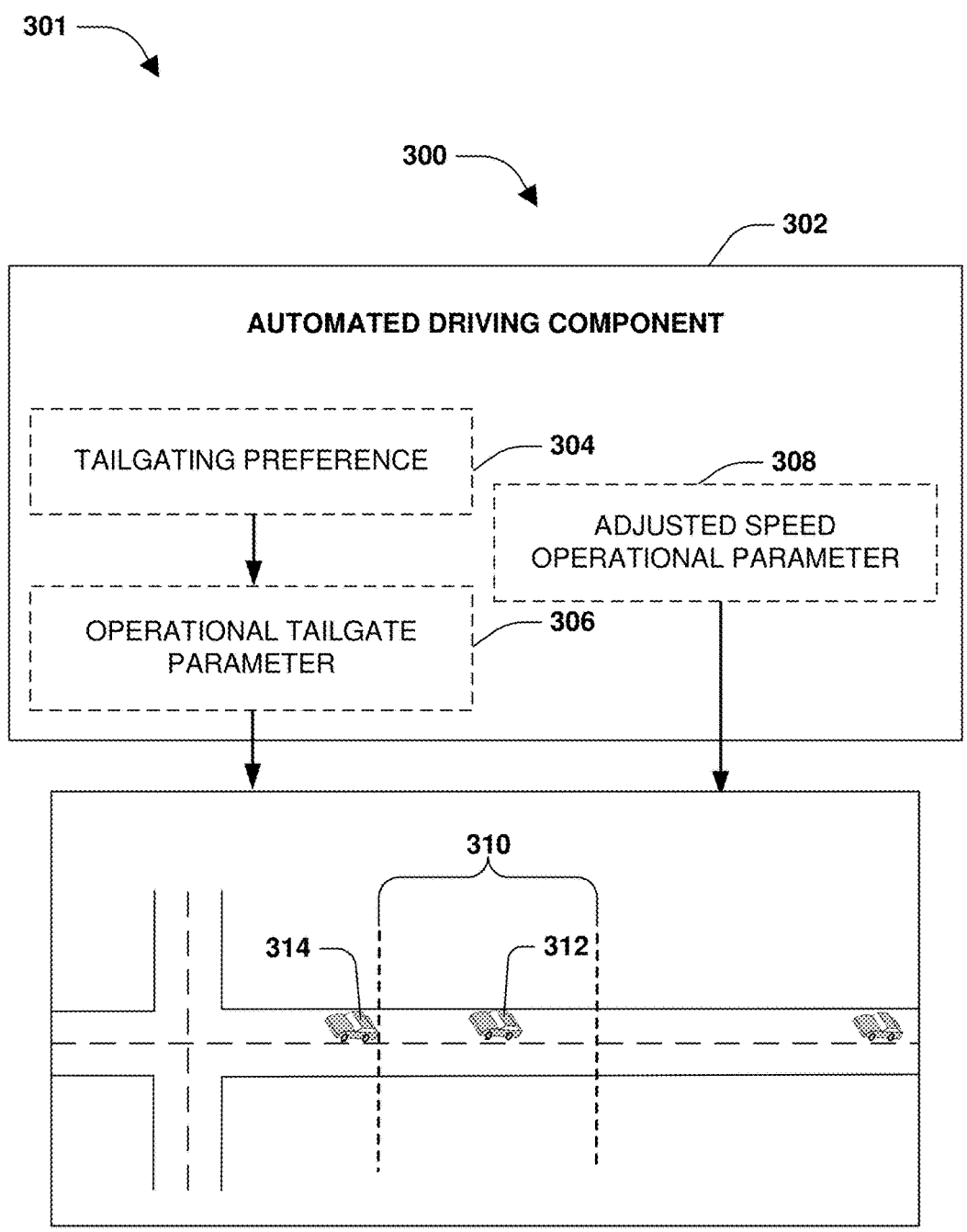
FIG. 3A is component block diagram illustrating an exemplary system for operating an autonomous vehicle, where the autonomous vehicle is within a tailgating threshold distance of a second vehicle.
Figure 3B:
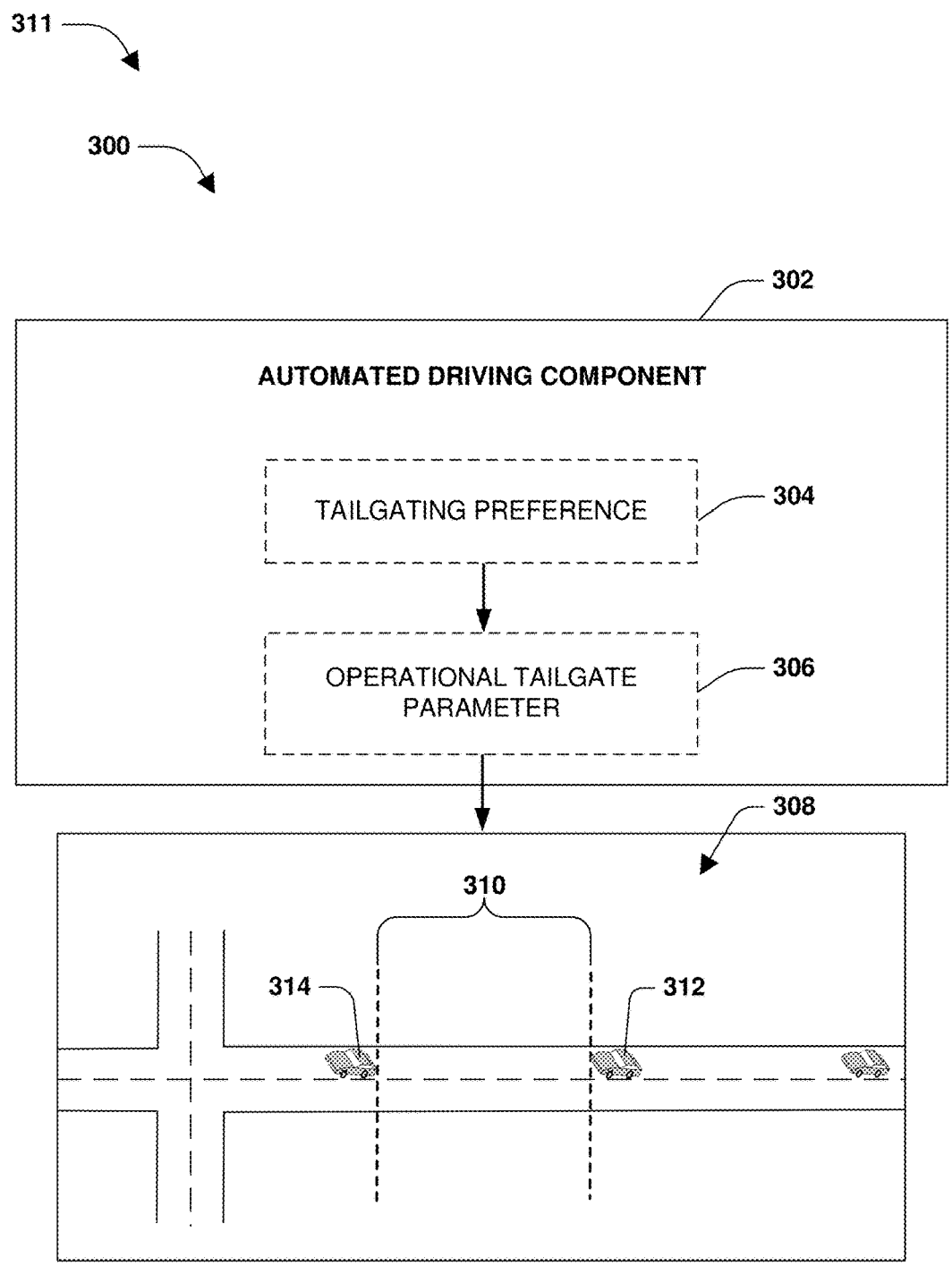
FIG. 3B is component block diagram illustrating an exemplary system for operating an autonomous vehicle, where the autonomous vehicle is not within a tailgating threshold distance of a second vehicle.

FIGS. 3A-3B illustrate examples of a system 300 for operating an autonomous vehicle 312, wherein a tailgating preference 304 has been provided. The system 300 may comprise an automated driving component 302. The automated driving component 302 may be configured to generate an operational tailgate parameter 306 for the autonomous vehicle 312 based upon the tailgating preference 304. The operational tailgate parameter 306 may determine a tailgate threshold distance 310. The tailgate threshold distance 310 may be a distance maintained between the autonomous vehicle 312 and a second vehicle 314 during operation of the autonomous vehicle 312. In an example, the tailgate threshold distance 310 may be a function of the speed of the autonomous vehicle 312 (e.g., the tailgate threshold distance 310 may increase as the speed of the autonomous vehicle 312 increases). FIG. 3A illustrates an example 301 of the autonomous vehicle 312 within the tailgate threshold distance 310. In an example, the autonomous vehicle 312 may enter into the tailgate threshold distance 310 when the speed of the second vehicle 314 decreases. Responsive to the autonomous vehicle 312 being within the tailgate threshold distance 310, the automated driving component 302 may adjust a speed operational parameter 308 to reduce the operating speed of the autonomous vehicle 312 (e.g., the throttle may be reduced and/or a braking mechanism of the autonomous vehicle 312 may be engaged). FIG. 3B illustrates and example 311 of the autonomous vehicle 312 being outside of the tailgate threshold distance 310 in response to adjusting the operating speed of the autonomous vehicle 312 based upon the adjustment to the speed operational parameter 308. In an example, once the autonomous vehicle 312 is outside of the tailgate threshold distance 310, the speed operational parameter 308 may be adjusted such that the operational speed of the autonomous vehicle 312 matches the speed of the second vehicle 314.

Figure 4:
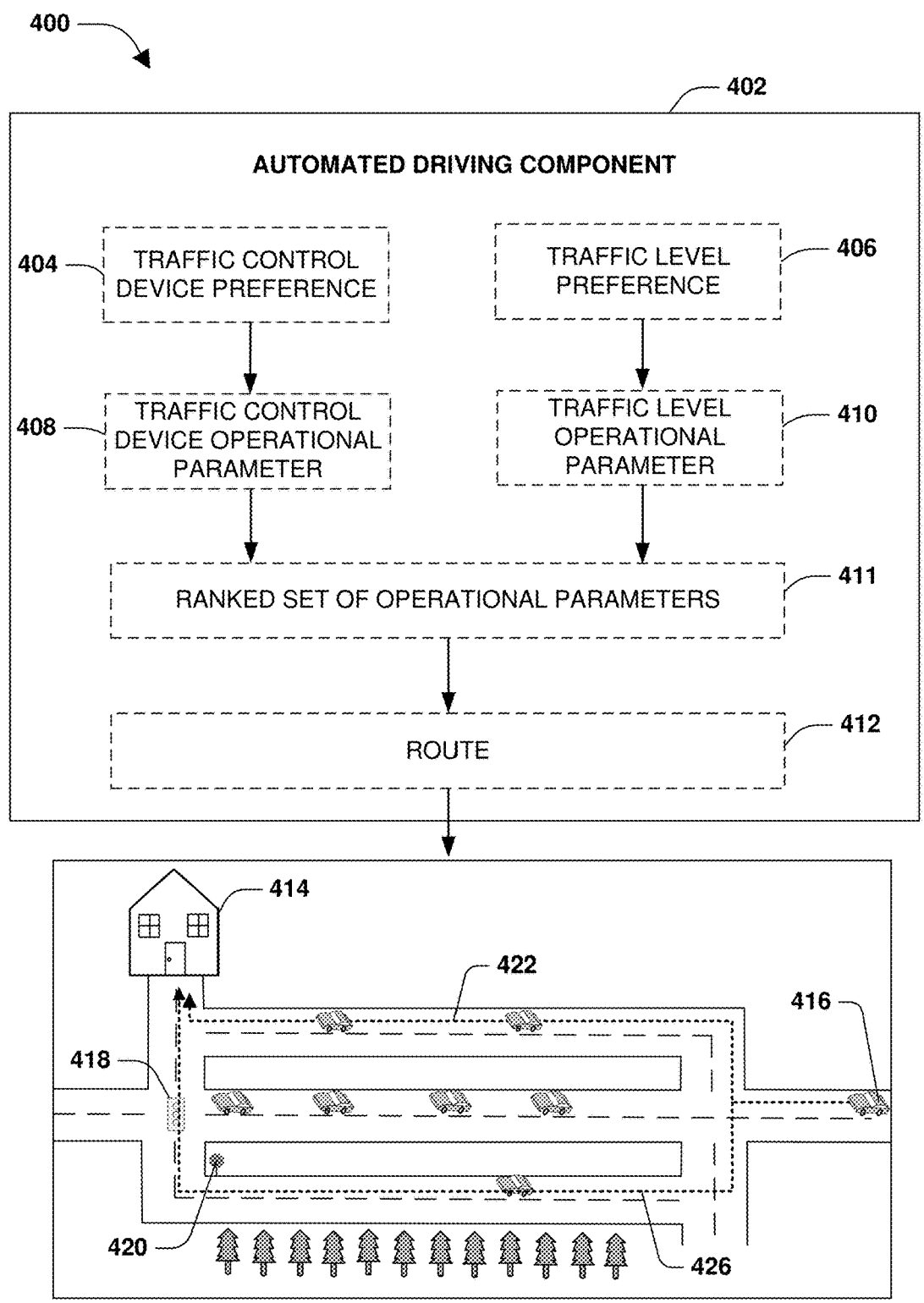
FIG. 4 is a component block diagram illustrating an exemplary system for operating an autonomous vehicle, where a route is generated from a ranked set of operational parameters.

FIG. 4 illustrates an example of a system 400 for operating an autonomous vehicle 416. The system 400 may comprise an automated driving component 402. A traffic control device preference 404 and a traffic level preference 406 may be provided to the automated driving component 402. The automated driving component 402 may be configured to generate a traffic control device operational parameter 408 based upon the traffic control device preference 404. The automated driving component 402 may be configured to generate a traffic level operational parameter 410 based upon the traffic level preference 406. The traffic control device operational parameter 408 and the traffic level operational parameter 410 may be ranked based upon priority value to generate a ranked set of operational parameters 411. In an example, the operational parameters 408-410 may be ranked based upon the relevance of an individual operational parameter to an objective, such as of a user and/or a profile (e.g., speed objective, a safety objective, a performance objective, a relaxation objective, etc.). A route 412 to a destination 414 may be generated based upon the ranked set of operational parameters 411. In an example, the generation of the route 412 may favor an operational parameter with a highest priority value. For example, responsive to the traffic control device operational parameter 408 having a higher priority value than the traffic level operational parameter 410, the route 412 may follow a first path 422 based upon the first path 422 avoiding traffic light 418 and stop sign 420, even though path 426 has slightly less traffic than path 422.

Figure 5A:
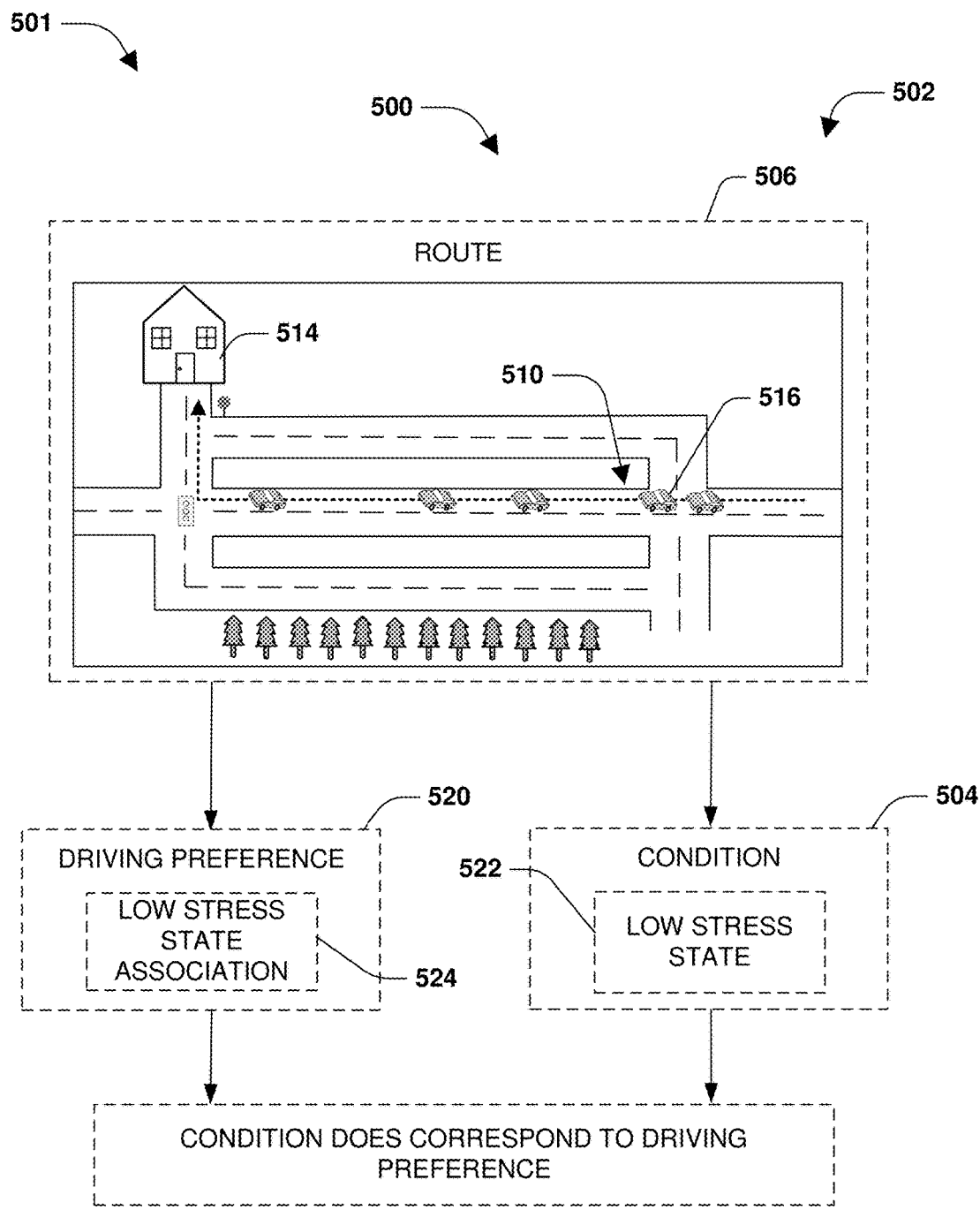
FIG. 5A is a component block diagram illustrating an exemplary system for operating an autonomous vehicle, where a condition of a user within the autonomous vehicle is determined.
Figure 5B:
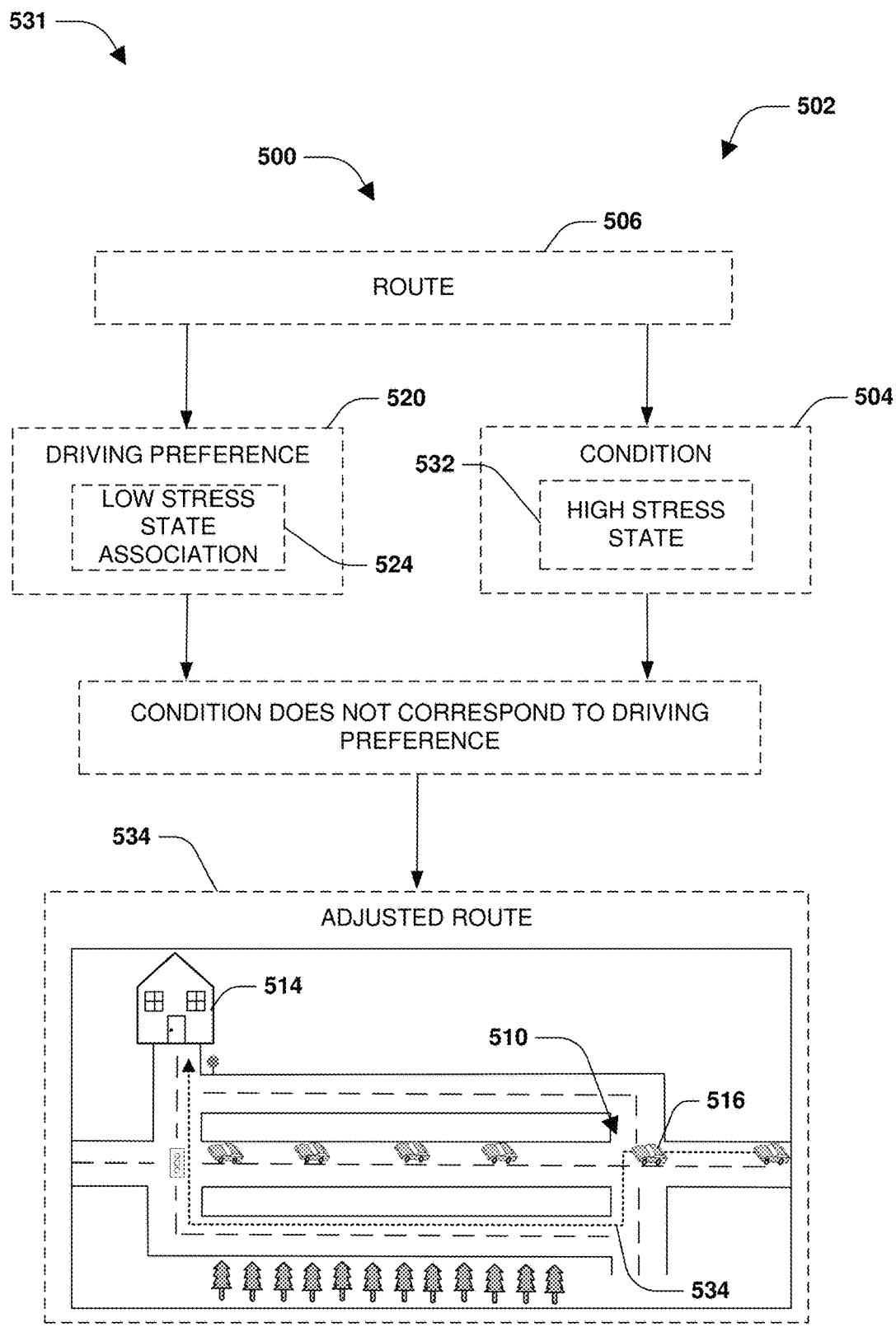
FIG. 5B is a component block diagram illustrating an exemplary system for operating an autonomous vehicle, where an adjusted route is generated based upon a condition of the user.

FIGS. 5A-5B illustrate examples of a system 500 for operating an autonomous vehicle 516, where a condition 504 of a user within the autonomous vehicle 516 is determined. The system 500 may comprise an automated driving component 502. The automated driving component 502 may be configured to generate a route 506 to a destination 514 based upon a driving preference 520 and/or an operational parameter (not illustrated). The route 506 may be configured to travel through a high traffic area 510. The driving preference 520 may be associated with a low stress state 524 for the user. FIG. 5A illustrates an example 501 where the condition 504 of the user in the autonomous vehicle 516 comprises a low stress state 522. The condition 504 may be determined by evaluating biometric data for the user traveling along the route 506. Responsive to the condition 504 of the user corresponding to the driving preference 520, the automated driving component 502 may continue to operate the autonomous vehicle 514 along the route 506. FIG. 5B illustrates an example 531 where the condition 504 of the user comprises a high stress state 532. In an example, the user may be experiencing the high stress state 532 as a result of traveling through the high traffic area 510 of the route 506. Responsive to condition 504 of the user not corresponding to the driving preference 520 of the low stress state 524, the automated driving component 502 may generate an adjusted route 534. In an example, the adjusted route 534 may be configured to lower the stress state of the user (e.g., avoid traffic, travel along a scenic route, etc.). By monitoring the condition 504 of the user during the operation of the autonomous vehicle 516 and adjusting the operation of the autonomous vehicle 516 accordingly, which may improve the physical and mental wellness of the user (e.g., a state of stress may be reduced) and/or a user experience associated with the autonomous vehicle 516.

Figure 6A:
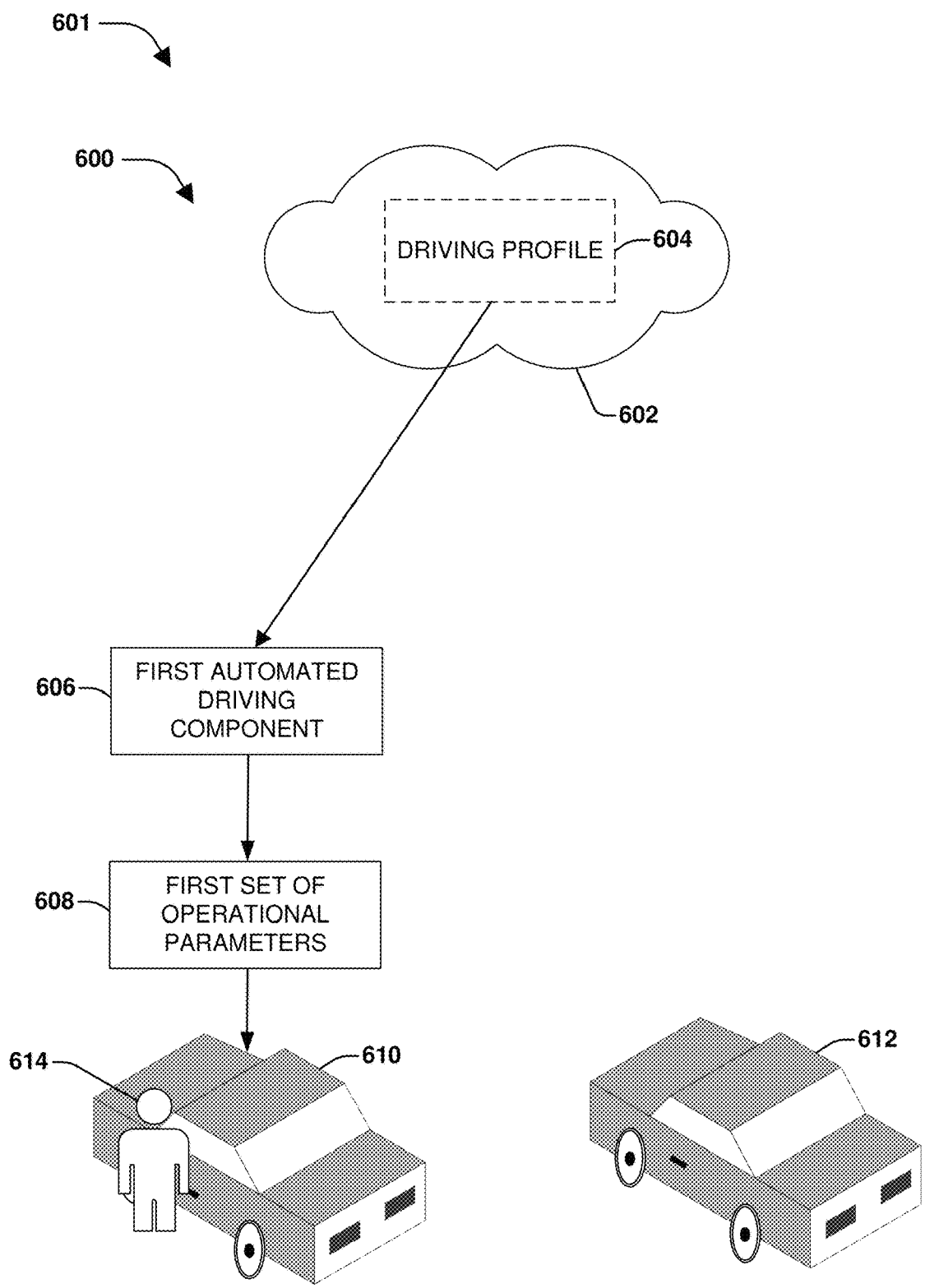
FIG. 6A is a component block diagram illustrating an exemplary system for operating an autonomous vehicle, where a driving profile is provided to a first autonomous vehicle and not a second autonomous vehicle based upon a user entering the first autonomous vehicle.
Figure 6B:
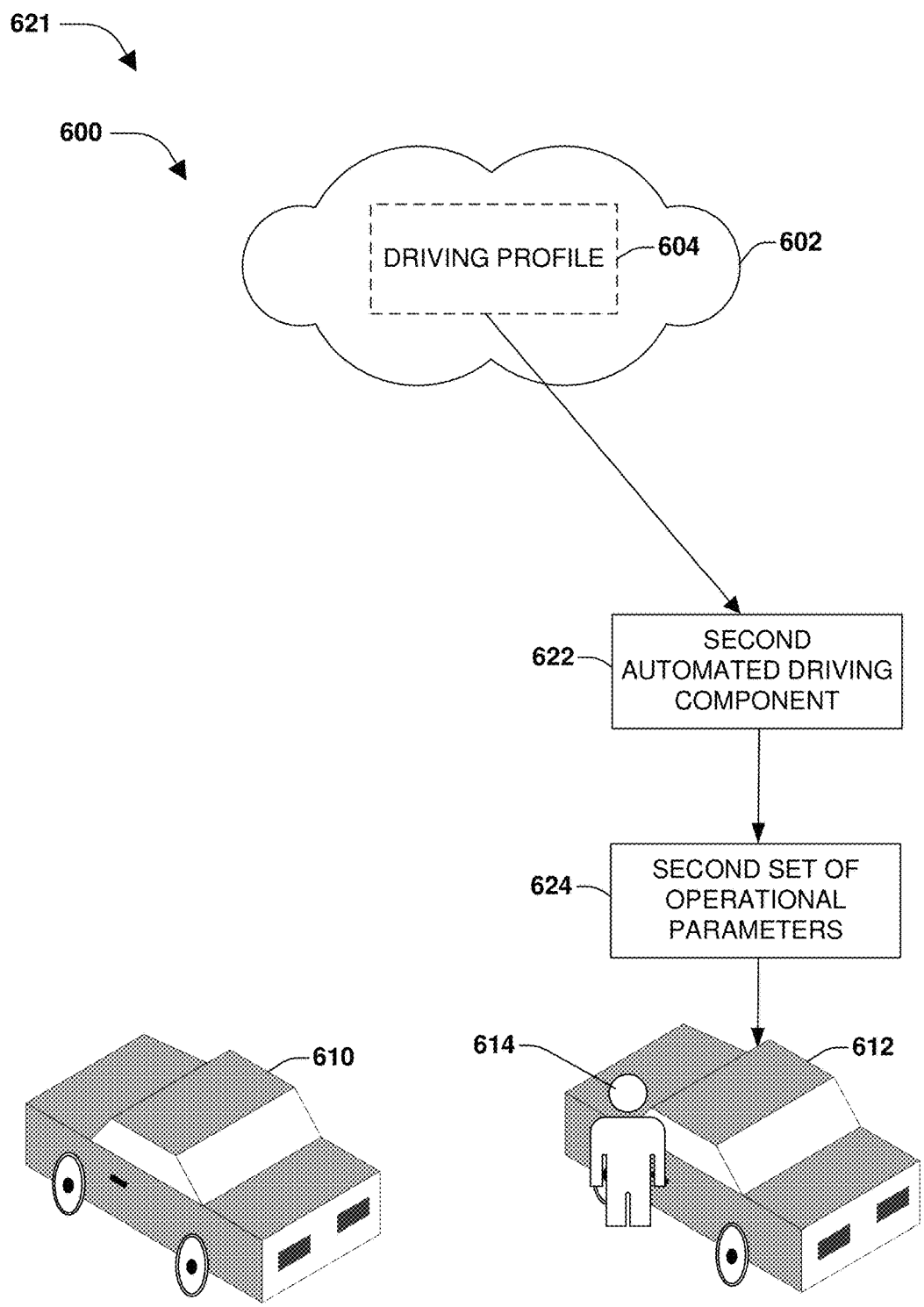
FIG. 6B is a component block diagram illustrating an exemplary system for operating an autonomous vehicle, where a driving profile is provided to a second autonomous vehicle and not a first autonomous vehicle based upon a user entering the second autonomous vehicle.

FIGS. 6A-6B illustrate examples of a system 600 for providing a first autonomous vehicle 610 and/or a second autonomous vehicle 612 with a driving profile 604 based upon which autonomous vehicle 610-612 a user 614 enters. The system 600 may be associated with a remote preference provider component 602, a first automated driving component 606 of the first autonomous vehicle 610, and/or a second automated driving component 622 of the second autonomous vehicle 612. FIG. 6A illustrates an example 601 where the user 614 is entering the first autonomous vehicle 610 and not the second autonomous vehicle 612. Responsive to the user 614 entering the first autonomous vehicle 610, the remote preference provider component 602 may provide the driving profile 604 to the first automated driving component 606. The first automated driving component 606 may generate a first set of operational parameters 608 for the first autonomous vehicle 610 based upon the driving profile 604. The first set of operational parameters 608 may be configured based upon a first set of characteristics of the first autonomous vehicle 610. The first autonomous vehicle 610 may be operated by the first automated vehicle component 606 based upon the first set of operational parameters 608. FIG. 6B illustrates an example 621 where the user 614 is entering the second autonomous vehicle 612 and not the first autonomous vehicle 614. Responsive to the user 614 entering the second autonomous vehicle 612, the remote preference provider component 602 may provide the driving profile 604 to the second automated driving component 622. The second automated driving component 622 may generate a second set of operational parameters 624 for the second autonomous vehicle 612 based upon the driving profile 604. The second set of operational parameters 624 may be configured based upon a second set of characteristics of the second autonomous vehicle 612. The second autonomous vehicle 612 may be operated by the second automated vehicle component 622 based upon the second set of operational parameters 624. In this way, driving profiles and/or driving preferences of a user, once created, may be efficiently and effectively provided to multiple autonomous vehicles (e.g., rented autonomous vehicles, etc.).

Figure 7:
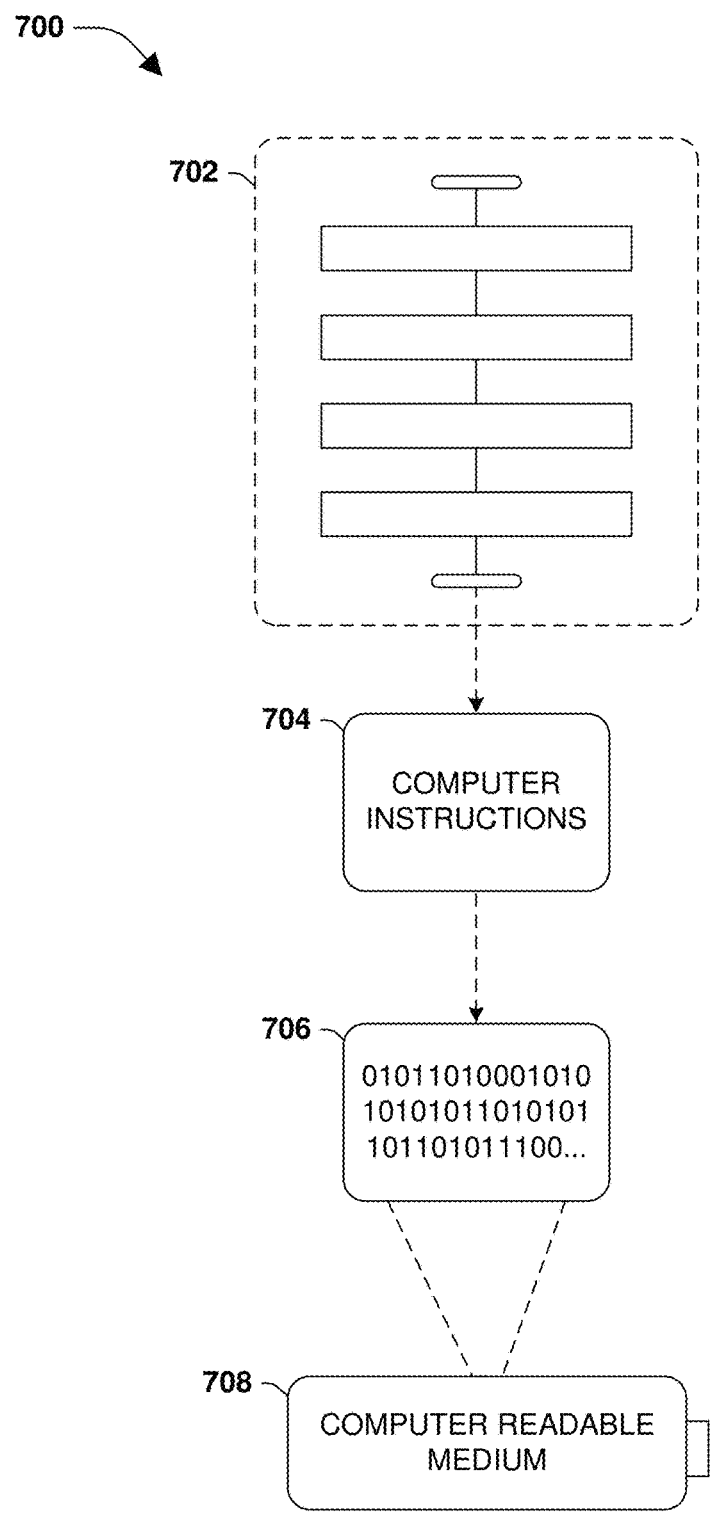
FIG. 7 is an illustration of an exemplary computer readable medium wherein processor-executable instructions configured to embody one or more of the provisions set forth herein may be comprised.

Still another embodiment involves a computer-readable medium comprising processor-executable instructions configured to implement one or more of the techniques presented herein. An example embodiment of a computer-readable medium or a computer-readable device is illustrated in FIG. 7, wherein the implementation 700 comprises a computer-readable medium 708, such as a CD-R, DVD-R, flash drive, a platter of a hard disk drive, etc., on which is encoded computer-readable data 706. This computer-readable data 706, such as binary data comprising at least one of a zero or a one, in turn comprises a set of computer instructions 704 configured to operate according to one or more of the principles set forth herein. In some embodiments, the set of computer instructions 704 are configured to perform a method 702, such as at least some of the exemplary method 100 of FIG. 1, for example. In some embodiments, the set of computer instructions 704 are configured to implement a system, such as at least some of the exemplary system 200 of FIG. 2, at least some of the exemplary system 300 of FIGS. 3A-3B, at least some of the exemplary system 400 of FIG. 4, at least some of the exemplary system 500 of FIGS. 5A-5B, and/or at least some of the exemplary system 600 of FIGS. 6A-6B, for example. Many such computer-readable media are devised by those of ordinary skill in the art that are configured to operate in accordance with the techniques presented herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing at least some of the claims.

As used in this application, the terms "component," "module," "system", "interface", and/or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

FIG. 7 and the following discussion provide a brief, general description of a suitable computing environment to implement embodiments of one or more of the provisions set forth herein. The operating environment of FIG. 7 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined and/or distributed as desired in various environments.

Figure 8:
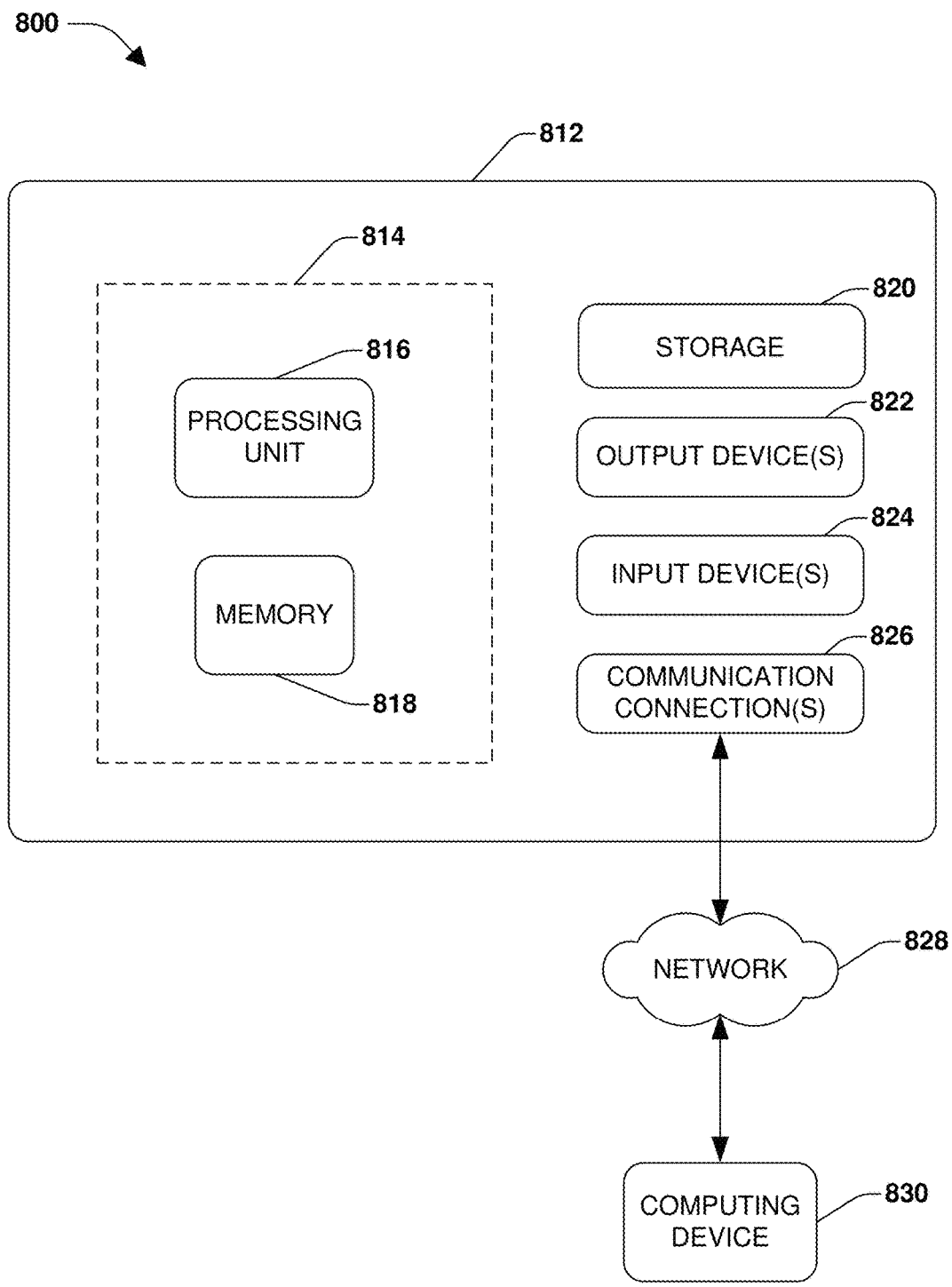
FIG. 8 is an illustration of an exemplary computing environment wherein one or more of the provisions set forth herein may be implemented.

FIG. 8 illustrates an example of a system 800 comprising a computing device 812 configured to implement one or more embodiments provided herein. In one configuration, computing device 812 includes at least one processing unit 816 and memory 818. Depending on the exact configuration and type of computing device, memory 818 may be volatile (such as RAM, for example), non-volatile (such as ROM, flash memory, etc., for example), or some combination of the two. This configuration is illustrated in FIG. 8 by dashed line 814.

In other embodiments, device 812 may include additional features and/or functionality. For example, device 812 may also include additional storage (e.g., removable and/or non-removable) including, but not limited to, magnetic storage, optical storage, and the like. Such additional storage is illustrated in FIG. 8 by storage 820. In one embodiment, computer readable instructions to implement one or more embodiments provided herein may be in storage 820. Storage 820 may also store other computer readable instructions to implement an operating system, an application program, and the like. Computer readable instructions may be loaded in memory 818 for execution by processing unit 816, for example.

The term "computer readable media" as used herein includes computer storage media. Computer storage media includes volatile and nonvolatile, removable and non-removable media implemented in any method or technology for storage of information such as computer readable instructions or other data Memory 818 and storage 820 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 812. Computer storage media does not, however, include propagated signals Rather, computer storage media excludes propagated signals Any such computer storage media may be part of device 812.

Device 812 may also include communication connection(s) 826 that allows device 812 to communicate with other devices. Communication connection(s) 826 may include, but is not limited to, a modem, a Network Interface Card (NIC), an integrated network interface, a radio frequency transmitter/receiver, an infrared port, a USB connection, or other interfaces for connecting computing device 812 to other computing devices. Communication connection(s) 826 may include a wired connection or a wireless connection. Communication connection(s) 826 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device 812 may include input device(s) 824 such as keyboard, mouse, pen, voice input device, touch input device, infrared cameras, video input devices, and/or any other input device. Output device(s) 822 such as one or more displays, speakers, printers, and/or any other output device may also be included in device 812. Input device(s) 824 and output device(s) 822 may be connected to device 812 via a wired connection, wireless connection, or any combination thereof. In one embodiment, an input device or an output device from another computing device may be used as input device(s) 824 or output device(s) 822 for computing device 812.

Components of computing device 812 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device 812 may be interconnected by a network. For example, memory 818 may be comprised of multiple physical memory units located in different physical locations interconnected by a network.

Those skilled in the art will realize that storage devices utilized to store computer readable instructions may be distributed across a network. For example, a computing device 830 accessible via a network 828 may store computer readable instructions to implement one or more embodiments provided herein. Computing device 812 may access computing device 830 and download a part or all of the computer readable instructions for execution. Alternatively, computing device 812 may download pieces of the computer readable instructions, as needed, or some instructions may be executed at computing device 812 and some at computing device 830.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein. Also, it will be understood that not all operations are necessary in some embodiments.

Further, unless specified otherwise, "first," "second," and/or the like are not intended to imply a temporal aspect, a spatial aspect, an ordering, etc. Rather, such terms are merely used as identifiers, names, etc. for features, elements, items, etc. For example, a first object and a second object generally correspond to object A and object B or two different or two identical objects or the same object.

Moreover, "exemplary" is used herein to mean serving as an example, instance, illustration, etc., and not necessarily as advantageous. As used herein, "or" is intended to mean an inclusive "or" rather than an exclusive "or". In addition, "a" and "an" as used in this application are generally be construed to mean one or more unless specified otherwise or clear from context to be directed to a singular form. Also, at least one of A and B and/or the like generally means A or B and/or both A and B. Furthermore, to the extent that "includes", "having", "has", "with", and/or variants thereof are used in either the detailed description or the claims, such terms are intended to be inclusive in a manner similar to the term "comprising".

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A method for operating an autonomous vehicle, comprising:
   providing a driving preference for a user to an automated driving component, implemented via a processor, of an autonomous vehicle;
   generating an operational parameter for the autonomous vehicle based upon the driving preference;
   operating the autonomous vehicle based upon the operational parameter;
   determining a condition of the user traveling in the autonomous vehicle based upon biometric data corresponding to the user while the autonomous vehicle is travelling; and
   responsive to the condition of the user not corresponding to the driving preference, adjusting the operational parameter for the autonomous vehicle.

2. The method of claim 1, the providing the driving preference comprising:
   creating a communication connection to a remote preference provider; and
   obtaining the driving preference, through the communication connection, from the remote preference provider.

3. The method of claim 2, the remote preference provider hosted on at least one of a cloud-based server or a mobile device of the user.

4. The method of claim 1, the driving preference comprising an aesthetic route preference, wherein the generating the operational parameter for the autonomous vehicle based upon the driving preference comprises generating the operational parameter for the autonomous vehicle based upon the aesthetic route preference.

5. The method of claim 1, the driving preference comprising a safe route preference, wherein the generating the operational parameter for the autonomous vehicle based upon the driving preference comprises generating the operational parameter for the autonomous vehicle based upon the safe route preference.

6. The method of claim 1, the biometric data comprising at least one of heartrate data, body temperature data, skin conductance data, voice stress level data, brainwave data, or blood alcohol level data.

7. The method of claim 1, comprising:
   generating a route to a destination based upon the driving preference, wherein the operating the autonomous vehicle based upon the operational parameter comprises operating the autonomous vehicle to travel the route based upon the operational parameter.

8. The method of claim 7, comprising:
   responsive to the condition of the user not corresponding to the driving preference, generating an adjusted route to the destination based upon the driving preference; and
   operating the autonomous vehicle to travel the adjusted route.

9. The method of claim 1, comprising:
   identifying that the user has entered a second autonomous vehicle;
   providing the driving preference to a second automated driving component, implemented via a second processor, of the second autonomous vehicle;
   generating a second operational parameter for the second autonomous vehicle based upon the driving preference; and
   operating the second autonomous vehicle based upon the second operational parameter.

10. The method of claim 1, the providing the driving preference comprising:
    selecting a driving profile comprising the driving preference; and
    evaluating the driving profile to identify the driving preference.

11. The method of claim 10, comprising:
identifying a second driving preference from the driving profile; and
generating a set of operational parameters based upon the driving preference and the second driving preference, wherein the set of operational parameters comprises the operational parameter and the operating the autonomous vehicle based upon the operational parameter comprises operating the autonomous vehicle based upon the set of operational parameters.

12. The method of claim 11, comprising:
determining a priority value for operational parameters within the set of operational parameters; and
ranking the operational parameters within the set of operational parameters based upon the priority values to generate a ranked set of operational parameters, wherein the operating the autonomous vehicle based upon the set of operational parameters comprises operating the autonomous vehicle based upon the ranked set of operational parameters.

13. The method of claim 1, the driving preference comprising a traffic control device preference, wherein the generating the operational parameter for the autonomous vehicle based upon the driving preference comprises generating the operational parameter for the autonomous vehicle based upon the traffic control device preference.

14. The method of claim 1, comprising:
selecting a cautious driving profile, wherein:
the providing the driving preference comprises evaluating the cautious driving profile to identify a tailgating preference, the tailgating preference corresponding to the driving preference,
the generating the operational parameter for the autonomous vehicle based upon the driving preference comprises generating an operational tailgate distance parameter for the autonomous vehicle based upon the tailgating preference, the operational tailgate distance parameter corresponding to the operational parameter, and
the operating the autonomous vehicle based upon the operational parameter comprises operating the autonomous vehicle based upon the operational tailgating distance parameter to maintain a tailgating distance.

15. The method of claim 10, the selecting the driving profile comprising:
accessing at least one of a calendar, an email client, a webpage, a social profile, or a mobile application of the user to identify an event of the user;
identifying event information corresponding to the event; and
evaluating the event information to select the driving profile.

16. The method of claim 1, comprising:
receiving feedback from the user corresponding to the operation of the autonomous vehicle;
evaluating the feedback to determine if the autonomous vehicle is operating in accordance with the driving preference; and
responsive to determining that the autonomous vehicle is not operating in accordance with the driving preference, adjusting the operational parameter for the autonomous vehicle.

17. A computer readable medium comprising instructions which when executed perform a method for operating an autonomous vehicle, comprising:
providing a driving preference for a user to an automated driving component, implemented via a processor, of an autonomous vehicle;
generating an operational parameter for the autonomous vehicle based upon the driving preference;
operating the autonomous vehicle based upon the operational parameter;
monitoring, based upon biometric data corresponding to the user while the autonomous vehicle is travelling, a condition of the user traveling in the autonomous vehicle;
responsive to the condition of the user not corresponding to the driving preference, adjusting the operational parameter for the autonomous vehicle; and
operating the autonomous vehicle based upon the adjusted operational parameter.

18. A system for operating an autonomous vehicle, comprising:
an automated driving component, implemented via a processor, configured to:
providing a driving preference for a user to an automated driving component, implemented via a processor, of an autonomous vehicle;
generating an operational parameter for the autonomous vehicle based upon the driving preference;
operating the autonomous vehicle based upon the operational parameter;
determining a condition of the user traveling in the autonomous vehicle based upon biometric data corresponding to the user while the autonomous vehicle is travelling; and
responsive to the condition of the user not corresponding to the driving preference, adjusting the operational parameter for the autonomous vehicle.

19. The system of claim 18 the automated driving component configured to operating the autonomous vehicle based upon the adjusted operational parameter.

20. The system of claim 18, the biometric data comprising at least one of heartrate data, body temperature data, skin conductance data, voice stress level data, brainwave data, or blood alcohol level data.

* * * * *